(12) United States Patent
Marx et al.

(10) Patent No.: US 12,251,557 B2
(45) Date of Patent: Mar. 18, 2025

(54) IMPLANTABLE ELECTRODE DEVICE AND METHOD OF FORMING AN IMPLANTABLE ELECTRODE DEVICE

(71) Applicant: CorTec GmbH, Freiburg (DE)

(72) Inventors: Andreas Marx, Freiburg (DE); Miguel Ulloa, Freiburg (DE)

(73) Assignee: CorTec GmbH, Freiburg (DE)

( * ) Notice: Subject to any disclaimer, the term of this patent is extended or adjusted under 35 U.S.C. 154(b) by 610 days.

(21) Appl. No.: 17/545,739

(22) Filed: Dec. 8, 2021

(65) Prior Publication Data

US 2022/0184385 A1    Jun. 16, 2022

(30) Foreign Application Priority Data

Dec. 10, 2020 (EP) ..................................... 20213156

(51) Int. Cl.
   *A61N 1/05*   (2006.01)

(52) U.S. Cl.
   CPC .................................. *A61N 1/0551* (2013.01)

(58) Field of Classification Search
   CPC .... A61N 1/0551; A61N 1/37205; A61N 1/05; A61N 1/0553; A61B 5/263; A61B 2562/0209; A61B 2562/04; A61B 5/294; A61B 5/6877
   See application file for complete search history.

(56) References Cited

U.S. PATENT DOCUMENTS

| | | | |
|---|---|---|---|
| 2006/0225274 A1* | 10/2006 | Greenberg | C23C 16/56 29/829 |
| 2011/0034977 A1* | 2/2011 | Janik | A61N 1/05 607/148 |
| 2012/0239126 A1 | 9/2012 | Zhou et al. | |
| 2013/0333918 A1* | 12/2013 | Lotfi | B29C 48/06 174/121 R |
| 2017/0203096 A1* | 7/2017 | Schibli | H01B 1/128 |
| 2018/0001081 A1 | 1/2018 | Minev et al. | |
| 2018/0345019 A1 | 12/2018 | Greenberg et al. | |

FOREIGN PATENT DOCUMENTS

WO    2018/015384 A1    1/2018

OTHER PUBLICATIONS

European Search Report issued for corresponding European Patent Application No. 20213156.1 dated May 18, 2021.
Suaning et al., "Fabrication of multi-layer, high-density microelectrode arrays for neural stimulation and bio-signal recording," Proceedings of he 3rd International IEEE EMBS Conference on Neural Engineering, pp. 5-8, IEEE, May 1, 2007, Piscataway, NJ, USA.

* cited by examiner

*Primary Examiner* — Mark W. Bockelman
(74) *Attorney, Agent, or Firm* — Myers Wolin, LLC (57) ABSTRACT

An implantable electrode device is provided comprising a first layer and a second layer, the second layer being on top of the first layer and including at least one electrode contact. The at least one electrode contact is exposable to a nerve of a nervous tissue of a human or of an animal. A connecting means electrically connects the electrode contact, where the connecting means is made up of at least one conducting wire, and the conducting wire is arranged within the first layer and is fixed to the electrode contact.

10 Claims, 8 Drawing Sheets

Prior Art

IMPLANTABLE ELECTRODE DEVICE AND METHOD OF FORMING AN IMPLANTABLE ELECTRODE DEVICE

CROSS REFERENCE TO RELATED APPLICATIONS

This application claims priority to European Application No. 20 213 156.1, filed Dec. 10, 2020, the contents of which are incorporated by reference herein.

FIELD OF THE INVENTION

The present invention relates to an implantable electrode. Further, the present invention relates to a method of forming an implantable electrode.

BACKGROUND

Modern medical technology allows for interacting with the human or animal neural system, e.g., if body functions have been lost or in case of dysfunctions of organs so as to bridge or restore the latter. For this, implantable electrodes are used that are brought into contact with the respective nerves to be stimulated or sensed. For example, microelectrodes or multi-electrode arrays are known in prior art which comprise a plurality of such electrodes through which neural signals are supplied for stimulating nerves of a nervous tissue. Such implantable electrodes usually are flexible and are made from medical silicone, Parylene, or polyimide, and a metal foil which forms the electrode contacts to the nerves as well as the bond pads to the external wiring (connection means), and the conductor tracks between the sensor pads and the contact pads to the external wiring.

The conductor tracks which lead from contact pads contacting the respective nerves to bond pads that are connected to external wiring may be formed by means of a laser-structuring of a metal foil layer according to known technologies.

The conductor tracks are rather instable mechanically. Due to their fineness, they are very fragile and may break.

Therefore, it is an object of the present invention to provide an implantable electrode and a method of producing such an electrode which avoid the above described problems at least partially.

SUMMARY

This object is solved by an implantable electrode device having the features according to this disclosure and by a method of producing an implantable electrode device according to this disclosure.

Accordingly provided is an implantable electrode device, comprising
a first layer, and a second layer, the second layer being on top of the first layer and including at least one electrode contact, the at least one electrode contact being exposable to a nerve of a nervous tissue of a human or of an animal,
a connecting means which electrically connects the at least one electrode contact, wherein
the connecting means is made up of at least one conducting wire, the at least one conducting wire being arranged within the first layer and being fixed to the at least one electrode contact.

The at least one electrode contact is directly or indirectly exposable to the nerve. Indirectly means that there are other layers of biological tissues are in between.

That is, the conducting wire is guided to the respective electrode contact and fixed directly to the electrode contact. There is no other conductor path portion between the conducting wire and the electrode contact which is exposable to the nerve. In particular there is no elongated conductor path formed from a metal foil between the conducting wire and the electrode contact on the electrode device.

Advantageously, the at least one conducting wire may be arranged in a core included within the first layer.

Further advantageously, the core may have the form of a channel within the first layer, extending from a first opening in the first layer to a position underneath the at least one electrode contact.

Further advantageously, the at least one electrode contact is formed as at least one contact pad.

Yet further advantageously, the at least one conducting wire is fixed to the at least one electrode contact at a point located underneath the at least one electrode contact, i.e., underneath the at least one contact pad.

Yet further advantageously, the first layer has a first surface and a second surface, wherein the second layer is arranged on the first surface, and wherein the first opening is formed in the second surface of the first layer.

Still further advantageously, the at least one wire may be guided through the channel the first opening into a cable coupling the electrode with an interface unit.

Furthermore, a strain relief means may be arranged within the core and guided through the channel and the first opening into the cable and being fixed to the electrode and to the interface unit.

Hereby, the strain relief means may be one of a suture, a string, litz wires, or other elongated, flexible, high pull-strength element.

The strain relief may be provided for the complete electrical path that is continuously through the electrode to the electrode cable up to the interface unit at the other end of the cable.

Moreover, preferably, the substrate is made of a flexible material, in particular, of Parylene, silicone, or polyimide.

The implantable electrode device may be formed as a micro-electrode array.

The core may comprise a filling material made from silicone.

The second layer may be made from a polymer, in particular from Parylene-C.

Further preferably, the core comprises a neutral fiber of the electrode device. The neutral fiber is a straight line which keeps its length constant when the device is bent along (i.e., in direction of) that line.

The implantable electrode may be formed as a micro-electrode array.

The micro-array may comprise a plurality of electrode contacts.

Thus, the configuration described provides an implantable electrode which consumes less space than configurations using conductor tracks known from prior art, since conductive wires are used which are guided inside the cavity provided in the second layer. Moreover, the wires are protected in the cavity which is filled with silicone and thus, is sealed. Also, the cavity provides for accommodating the strain relief means, namely, the suture inside the cavity which is guided through the entire electrode so as to uniformly and continuously ensure stress relief throughout the entire implantable electrode.

This disclosure further provides a method of forming an implantable electrode device, in particular according to any one of the preceding claims, the method comprising the steps:
- an intermediate layer, preferably from PVC, is applied onto a carrier substrate made preferably from ceramics;
- a first layer of medical silicone is applied by spin coating onto the intermediate layer;
- the first silicone layer is structured with a Laser to define a future first opening around its center axis, which center axis is perpendicular to the surface of the first layer;
- a sacrificial layer, preferably a Kapton band, is applied onto the structured first silicone layer;
- the sacrificial layer is Laser-structured to define a future cavity for a core;
- parts of the sacrificial layer which do not define the future cavity for the core are removed;
- the sacrificial layer and parts of the first silicone layer not covered by the sacrificial layer are covered with a second silicone layer, preferably by spin coating;
- the second silicone layer is pressed using, a foil, preferably a PTFE foil, placed onto the second layer, and cured in order to obtain a plane surface;
- after curing, the foil is removed;
- a third silicone layer is applied onto the second silicone layer, to form a bond coat;
- the third silicone layer is Laser-structured to define a future second opening and a future welding point above the second the opening;
- on the third silicone layer, a metal layer, preferably a platinum90-iridium10 foil, is laminated, and cured under pressure in order to keep its surface plane;
- The cured metal layer is Laser-structured to form at least one electrode contact;
- parts of the cured metal layer not forming the at least one electrode contact are removed;
- glue, preferably silicone glue, is applied as an annular structure onto the at least one electrode contact around a future welding point to be located underneath the at least one electrode contact;
- the annular structure on the at least one electrode contact is covered by a foil, in particular made from Kaptan;
- a second layer which preferably is a Parylene-C layer is applied, preferably by chemical vapor deposition;
- the second layer is Laser-structured to allow re-opening the at least one electrode contact;
- the at least one electrode contact is re-opened by removing parts of the second layer and the foil covering it;
- the substrate and the intermediate layer are removed, thus exposing the first opening to the future cavity for the core;
- the sacrificial layer and residential silicone particles are removed from the lower side, thus forming the cavity for the core;
- connecting means are laid out within the cavity for the core and welded to the at least one electrode contact;
- wires are welded to the pad contacts;
- a strain relief, preferably a suture, is laid out within the cavity;
- a point on the at least one contact opposite to the welding point is sealed with glue, preferably silicone glue;
- the cavity comprising the connecting wires and the strain relief is filled up and sealed with glue, preferably silicone glue, thus forming the core.

BRIEF DESCRIPTION OF THE DRAWING

In the following, the invention is described by means of embodiments and the drawing in further detail. In the drawings.

DETAILED DESCRIPTION OF THE PREFERRED EMBODIMENTS

Figure 1:
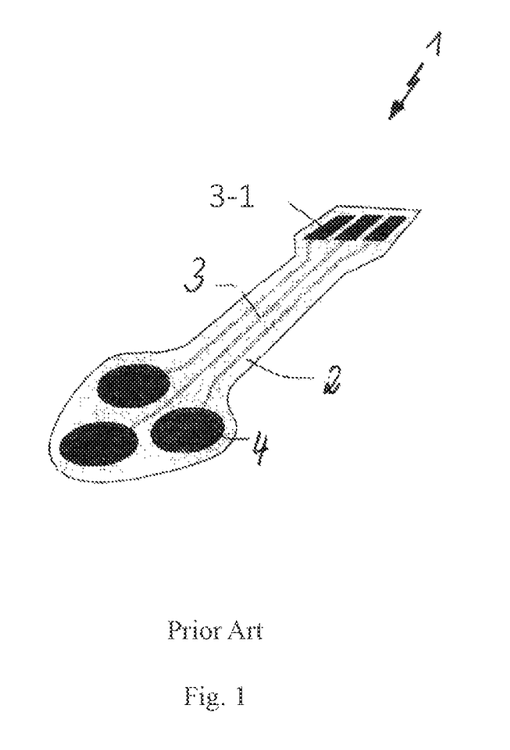
FIG. 1 shows a schematic perspective view of an implantable electrode according to prior art.

FIG. 1 shows a schematic perspective view of an implantable electrode 1 according to prior art. The electrode 1 comprises an electrically insulating substrate 2, which here is medical silicone, in which conductor paths 3 are embedded so as to connect electrode contacts or contact pads 4 to bond pads or terminal contacts 3-1, which in turn are connected to an electrode cable (not shown) connected to a power supply (not shown). The conductor paths 3 as well as the electrode contacts 4 and terminal contacts 3-1 may be produced by laser structuring of a metal foil, which is well known in the prior art.

Figure 2A:
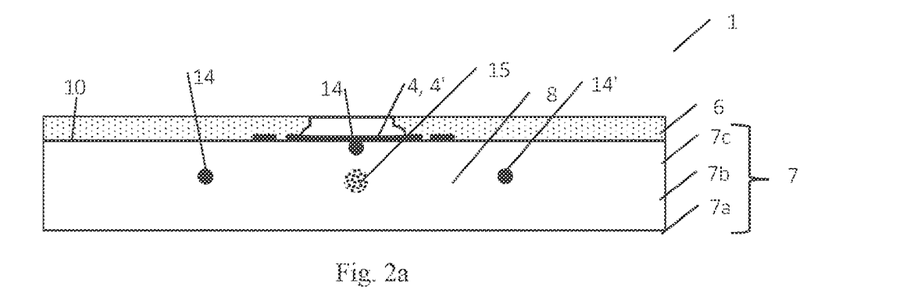
FIGS. 2a-c show an implantable electrode according to a first embodiment of the invention.

FIG. 2a is a cross-sectional view of an implantable electrode device 1 according to a first embodiment of the invention illustrating the sequence of layers of the implantable electrode device 1. As can be seen, the electrode device 1 basically is made up of a first layer 7; 7a 7b, 7c, and a second layer 6. The second layer 6 is arranged on a first surface 10 on top of the first layer 7, 7a 7b, 7c and includes at least one electrode contact 4, 4'. The at least one electrode contact 4, 4' is exposable directly or indirectly to nervous tissue of a human or of an animal. However, other layers of biological tissues might be in between.

The implantable electrode device 1 further comprises a connecting means which electrically connects the at least one electrode contact 4, 4' to the outside of the implantable electrode device 1. The connecting means is made up of at least one conducting wire 14, 14'. The at least one conducting wire 14, 14' is arranged within the first layer 7; 7a, 7b, 7c and is fixed to the at least one electrode contact 4, 4'.

Figure 2B:
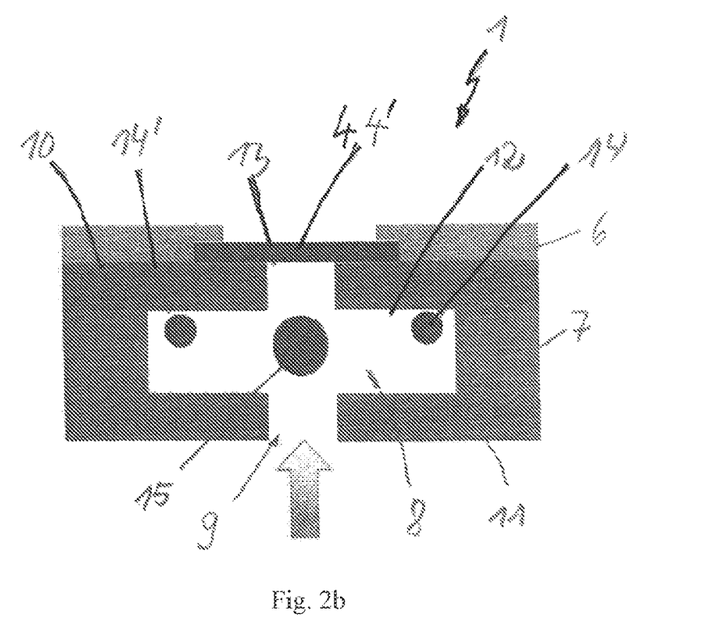

More specifically, the at least one conducting wire 14, 14' is guided up to the at least one contact 4, 4' and fixed directly to the at least one contact 4, 4' of the electrode device 1 on the backside of the at least one contact 4, 4'. The backside of the at least one contact 4, 4' is the side opposed to the side exposable to the nerve of the nervous tissue. There are no metal conductor portions on the electrode device 1 between the at least one contact 4, 4' and the at least one conducting wire 14, 14'. As can be seen in FIG. 2b and in FIGS. 4t to 4w, the location where the conducting wires are fixed to the at least one contact 4, 4' is at the (temporary) second opening 13 of the first silicon layer 7; 7b 7c. This is underneath the at least one electrode contact 4, 4'.

Fixation of the at least one conducting wire 14, 14' to the at least one contact 4, 4' is done e.g., by welding.

The electrode device 1 may further comprise a strain relief 15 for the at least one conducting wire 14, 14', which will be further described below.

The first layer 7 is made up of medical silicone material. The second layer 6 is a Parylene-C layer applied by chemical vapor deposition (CVP) on top of the first layer 7, in particular, on the first surface 10 of the first layer 7.

FIG. 2b is a cross-section of the implantable electrode 1 in an intermediate stage of production, illustrating how the at least one conducting wire 14, 14' is placed into the implantable electrode.

Hereto, the first layer 7 has a core 8 which is formed as a channel 12 extending from a first opening 9 formed in a second surface 11 of the first layer 7 to the location or locations of the at least one electrode contact 4, 4' through the electrode device 1. The second surface 11 is opposite to the first surface 10.

During production, the at least one conducting wire 14, 14' is placed in the core 8 within the implantable electrode 1. The core 8 is a zone in the interior of the first layer 7, i.e., the core 8 is enclosed by the first layer 7. Later during the production process, the core 8 (i.e., the hollow space) is filled up with silicon glue, thus fixing the wires 14, 14'.

The optional strain relief 15 (described below) is also placed in the channel 12 through the opening 9.

Figure 2C:
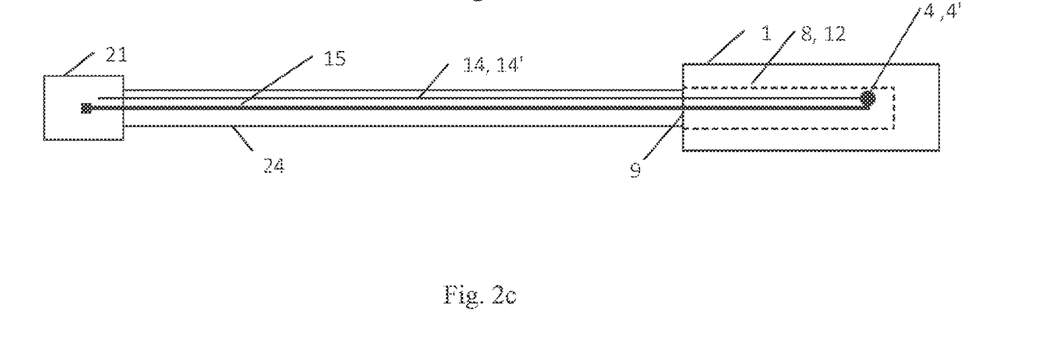

FIG. 2c illustrates the implantable electrode device 1 of the first embodiment of the present invention being electrically coupled with an interface unit 21 through the at least one conducting wire 14, 14'. The at least one conducting wire 14, 14' is guided within a cable 24. The cable 24 is flexible and comprises a tube made from e.g., silicone.

The interface unit 21 may be, or comprise, a plug and/or an electronic unit which processes signals from and/or to the electrode device 1. It may relay the signals from/to a remote location. The interface unit 21 is of course a unit physically distinct and separate from the electrode device 1.

The electrode device 1 may further comprise a strain relief 15 for the at least one conducting wire 14, 14', which is fixed to the electrode device 1 and guided within the cable 24 to the interface unit 21 and fixed there. Within the electrode device 1, the strain relief 15 is guided through the channel 12 comprised in the core 8. The strain relief 15 extends through the entire channel 12 and thus, basically through the entire electrode device 1 and serves as a strain relief means, as described above.

The strain relief 15 is guided through the core 8 in a way that ensures it is straight and under slight tension. Tensile stresses applied in axial direction of the electrode array will distribute between the wires and the suture with the suture taking more tensile load compared to the wires.

The strain relief 15 may be a suture. Instead of a suture 15, other flexible material that can withstand high pull forces (e.g., string, thread, litz wire, Kevlar filament, etc.) can be used as the strain relief means 15.

The strain relief 15 is placed into the electrode device 1 at the same time during production as the at least one conducting wire 14, 14', refer to the description thereof above. Since the entire core 8 is filled with silicone, the inner space accommodating the at least one conducting wire 14, 14' and the strain relief 15 is sealed.

Figure 3A:
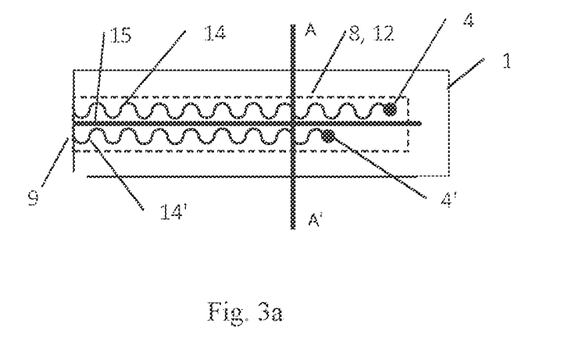
FIGS. 3a and b show a second embodiment of the invention.

FIG. 3a illustrates a second embodiment of the invention. While the at least one conducting wire 14, 14' is guided in meander form within the electrode device 1, the strain relief 15, i.e., the suture 15 is guided straight within the electrode device 1. This provides for the strain relief of the conducting wires 14, 14' within the electrode device 1.

Figure 3B:
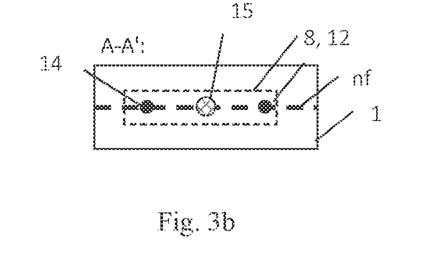

FIG. 3b illustrates a cross-section of the implantable electrode of FIG. 3a along a cut line A-A'. Preferably the core 8 is located around (i.e, comprises) the "neutral fiber" nf in the electrode device. The neutral fiber is a straight line which keeps its length constant when the device is bent along (i.e., in direction of) that line. On other words, the neutral fiber nf or neutral plane is the one plane within the electrode device 1, along which there are no longitudinal stresses or strains when the electrode device 1 is bent. That is, the fiber nf keeps its length constant when the electrode device 1 is bent. If the core 8 is around the neutral fiber nf, the conducting wires 14, 14' placed therein keep their lengths always constant.

By the configuration described above, a space saving arrangement is achieved which moreover provides for strain relief over the entire length of the implantable electrode device 1.

Figure 4A:
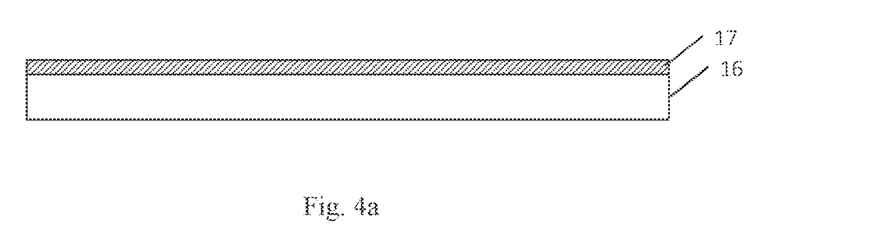
FIGS. 4a-w illustrate the steps of an exemplary production process for the implantable electrode according to the invention.
Figure 4B:
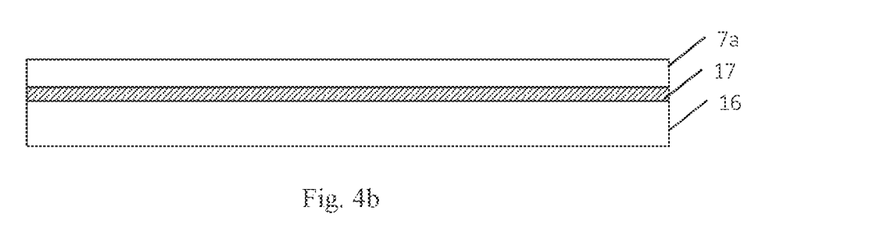
Figure 4C:
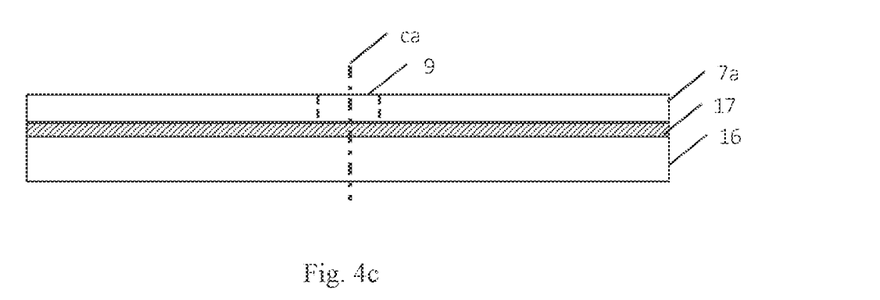
Figure 4D:
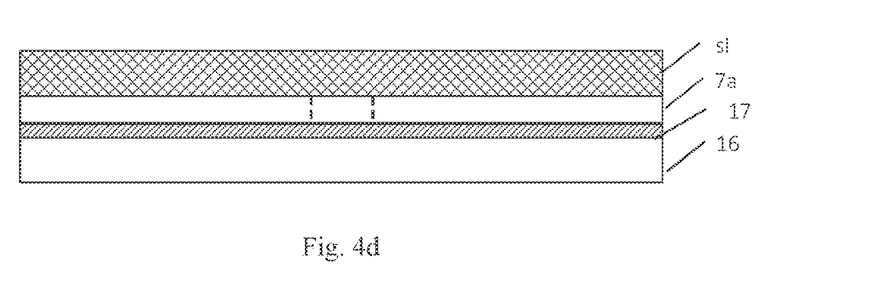
Figure 4E:
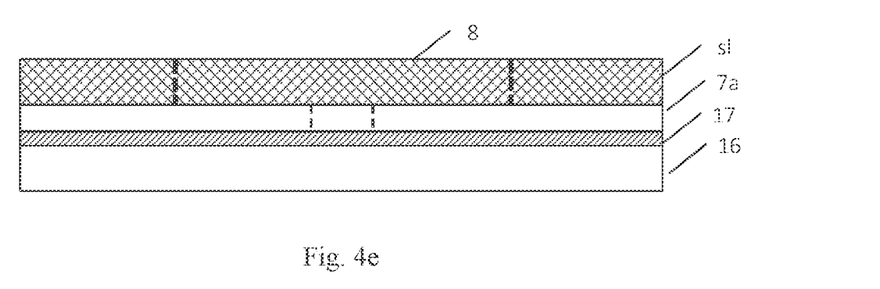
Figure 4F:
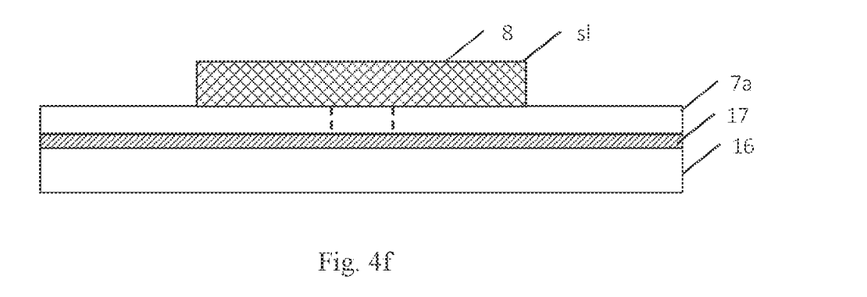
Figures 4G, 4H:
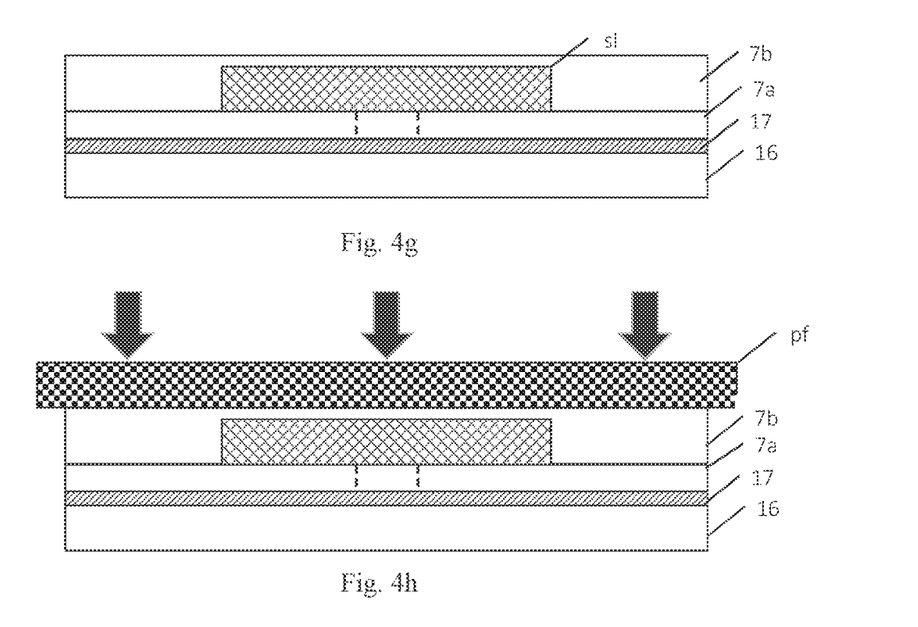
Figure 4I:
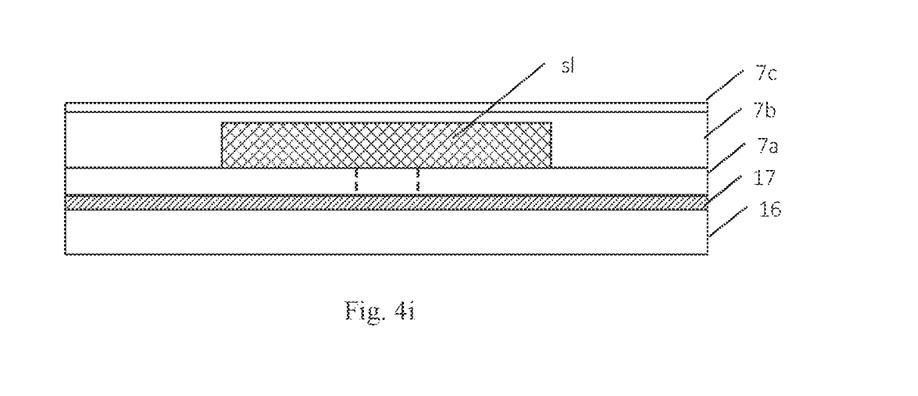
Figure 4J:
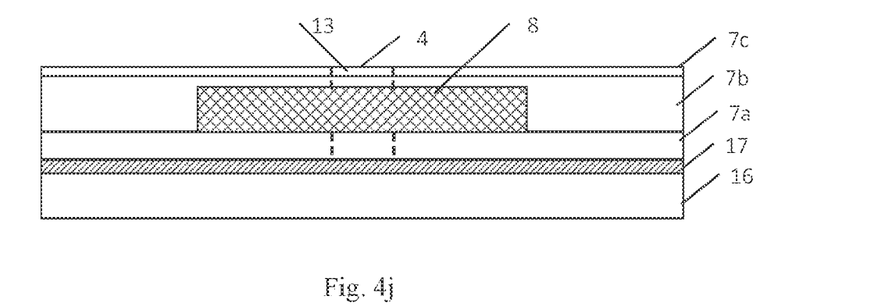
Figure 4K:
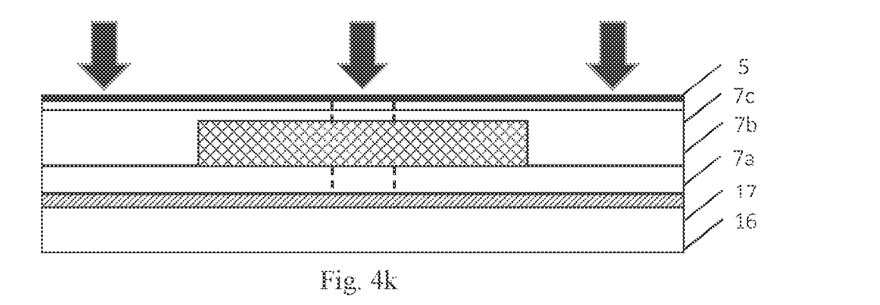
Figure 4L:
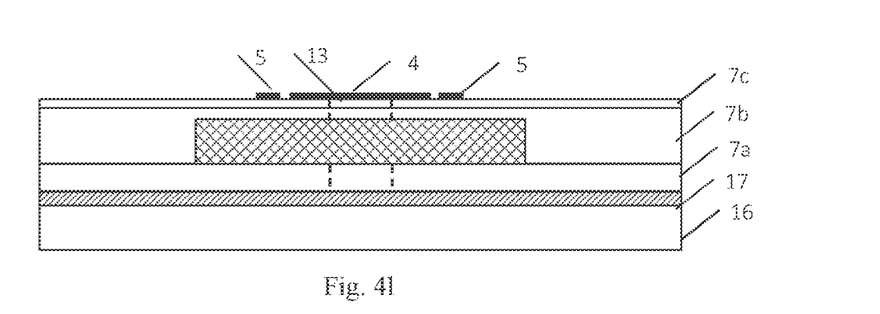
Figure 4M:
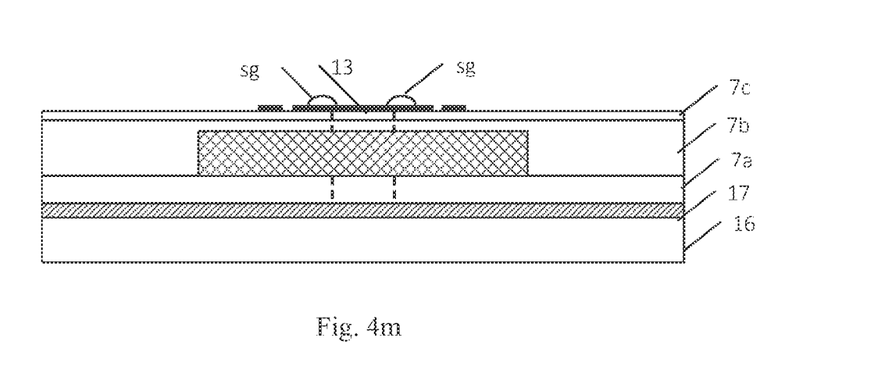
Figure 4N:
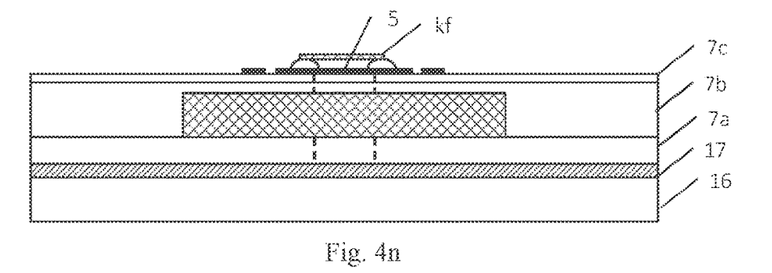
Figure 4O:
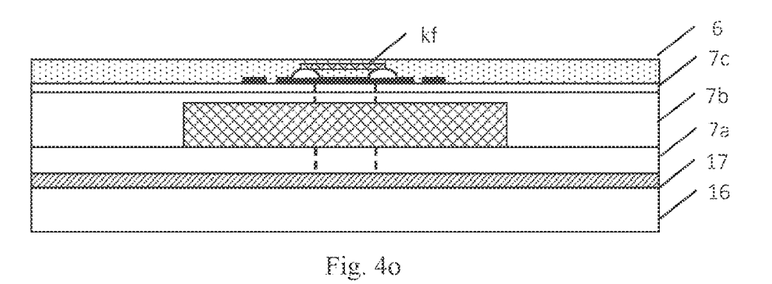
Figure 4P:
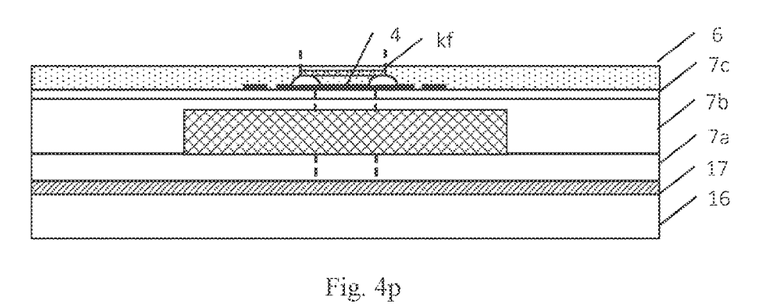
Figure 4Q:
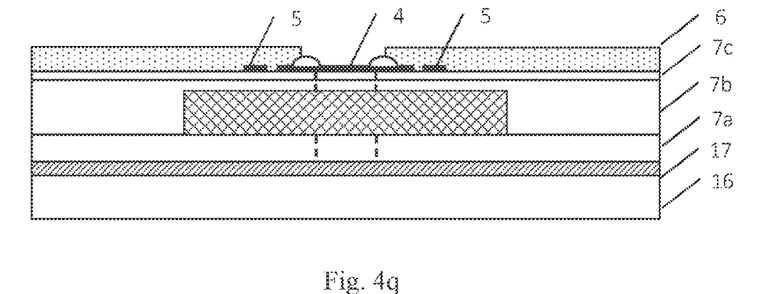
Figure 4R:
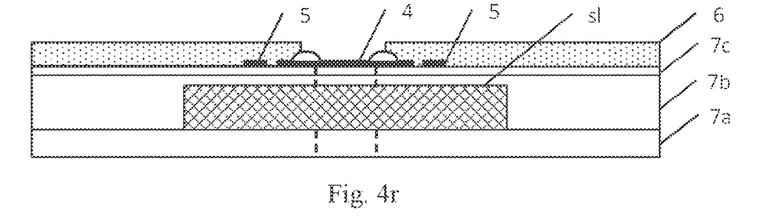
Figure 4S:
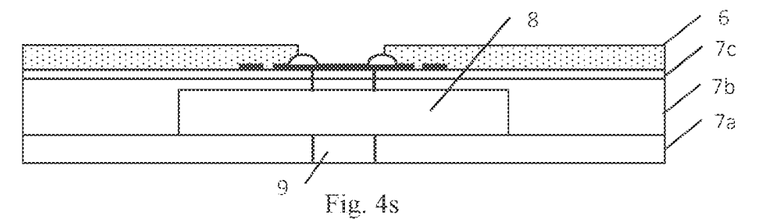
Figure 4T:
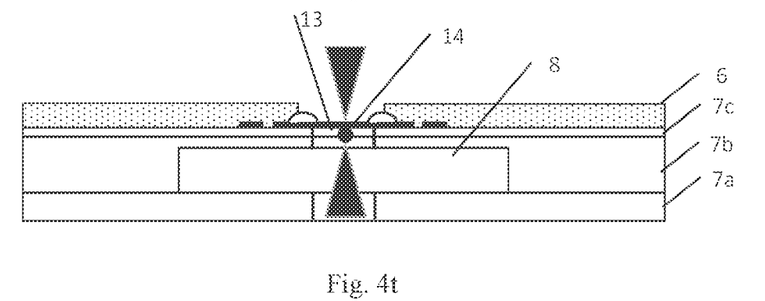
Figure 4U:
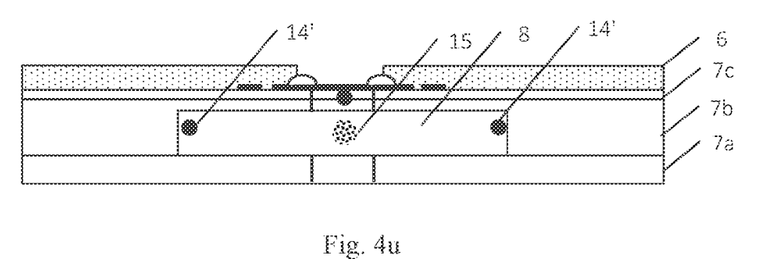
Figure 4V:
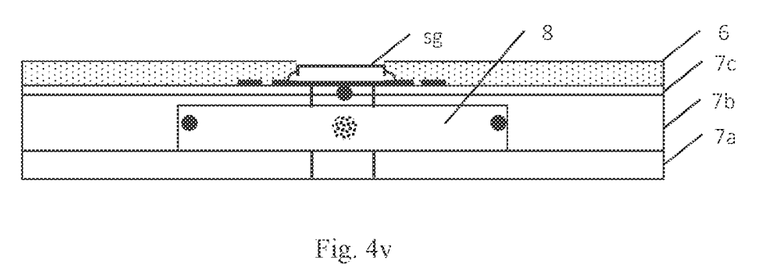
Figure 4W:
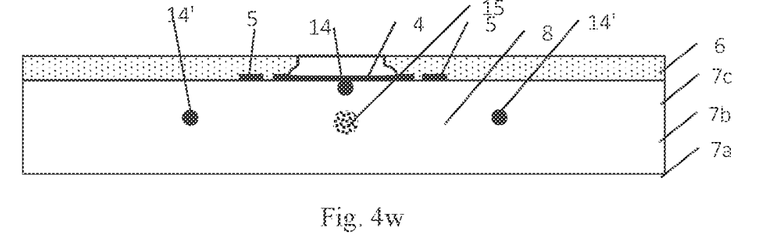

With reference to FIGS. 4a to 4w, a production process for the implantable electrode device 1 of the present invention is described step by step.

In a first step, refer to FIG. 4a, an intermediate polymeric release layer 17 is applied onto a carrier substrate 16 made e.g., from ceramics. The intermediate layer 17 separates the carrier substrate 16 from the layer 7a, and allows to remove the ceramic carrier substrate 16 along with itself later.

A first layer 7a of medical silicone is applied by spin coating onto the intermediate layer 17, refer to FIG. 4b.

Then, the first layer 7a is structured with a Laser to define a (future) first opening 9 around its center axis ca, which center axis ca is perpendicular to the surface of the first layer 7a, refer to FIG. 4c.

A (future) cavity for a core 8 will be prepared by applying sacrificial layer process making use of polyimide material, e.g., of a laser structured Kapton® band.

That is, the Kapton band as sacrificial layer sl is applied onto the structured first silicone layer 7a, refer to FIG. 4d.

The sacrificial layer sl is Laser-structured to define the geometry of the (future) cavity for the core 8, refer to FIG. 4e.

The parts of the sacrificial layer sl which do not define the geometry of the (future) cavity for the core 8 are removed, refer to FIG. 4f.

The sacrificial layer sl as well as the parts of the first silicone layer 7a not-covered by the sacrificial layer sl are covered with a second silicone layer 7b by spin coating, refer to FIG. 4g.

In order to obtain a plane surface, the second silicone layer 7b is pressed using a PTFE foil pf placed onto the second layer 7b during curing the silicone, refer to FIG. 4h. The PTFE foil is removed after curing.

As a bond coat, a third silicone layer 7c is applied onto the second silicone layer 7b, refer to FIG. 4i, and Laser-structured to define a (future) second opening 13 and a (future) welding point above the second opening 13, refer to FIG. 4j.

On the third silicone layer 7c, a metal layer 5, e.g., a platinum90-iridium10 foil, is laminated, and cured under pressure, refer to FIG. 4k, in order to keep its surface plane.

The cured metal layer 5 is then Laser-structured to form electrode contacts 4. Outer parts thereof not forming electrode contacts are removed, refer to FIG. 4l.

Silicone glue sg is applied in an annular shape around a (future) opening 13 for a future welding point, the opening 13 and welding point being underneath electrode contact 4, refer to FIG. 4m and FIG. 4t.

The location above the welding point is temporarily covered by a Kapton® foil kf, refer to FIG. 4n.

The metal layer 5 in turn is covered by the second layer 6 which is e.g., a Parylene-C layer 6 applied by chemical vapor deposition (CVD), refer to FIG. 4o.

The Parylene-C-layer 6 is Laser-structured to allow re-opening the welding point 4, refer to FIG. 4p.

The welding point 4 is opened by removing the parts of the Parylene layer 6 and Kapton foil kf covering it, refer to FIG. 4q.

Then, the carrier substrate 17 along with the intermediate polymeric release layer 16 is removed, thus exposing the first opening 9 to the sacrificial layer (sl) from the lower side, refer to FIG. 4r.

Then, the sacrificial layer sl and residential silicone particles are removed from the lower side, refer to FIG. 4s, thus forming the cavity (8) which corresponds to the future core 8.

Then, conducting wires i.e., the connecting means 14, 14' are laid out within the cavity (corresponding to core 8) and welded directly to the at least one electrode contact 4, 4', refer to FIG. 4t. The connecting means 14, 14' (e.g., a conducting wire) are welded to the rearward surface of the at least one electrode contact 4, 4', that is the side opposite to the side exposable to the nervous tissue, and at the location of the at least one electrode contact exposable to the nervous tissue.

Yet further, the strain relief, that is, the suture 15 is laid out within the cavity for the core 8, refer to FIG. 4u.

The point on the metal contact 4 opposite to the welding point is sealed with silicone glue sg, refer to FIG. 4v.

Finally, the cavity comprising the connecting wires 14, 14' and the strain relief suture 15 is filled up and sealed with silicone glue sg, thus forming the core 8, refer to FIG. 4w.

REFERENCE NUMERALS 1 implantable electrode
2 substrate
3 conductor path
3-1 terminal contact
4, 4' electrode contact
5 metal layer
6 second layer
7; 7a, 7b, 7c first layer
8 core, cavity
9 first opening
10 first surface of first layer
11 second surface of first layer
12 channel
13 second opening for (future) welding location
14, 14' connection means, conducting wire
15 strain relief means, suture
16 carrier substrate
17 intermediate layer
21 interface unit
24 cable
ca central axis
kf Kapton foil
of neutral fiber
pf PTFE foil
sg silicone glue
sl sacrificial layer

What is claimed is:

1. An implantable electrode device, comprising:
a first layer, and a second layer, the second layer being on top of the first layer and including at least one electrode contact, the at least one electrode contact being exposable to a nerve of a nervous tissue of a human or of an animal,
a connecting means which electrically connects the at least one electrode contact, wherein
the connecting means is made up of at least one conducting wire, the at least one conducting wire being arranged within the first layer and being fixed to the at least one electrode contact,
wherein the at least one conducting wire is arranged in a core included within the first layer, and
wherein the core has the form of a channel within the first layer, extending from a first opening in the first layer to a position underneath the at least one electrode contact,
wherein the at least one wire is guided through the channel and the first opening into a cable coupling the electrode with an interface unit,
wherein a strain relief means is arranged within the core and guided through the channel and the first opening into the cable and is fixed to the electrode and to the interface unit.

2. The implantable electrode device of claim 1, wherein the at least one electrode contact is formed as at least one contact pad.

3. The implantable electrode device of claim 2, wherein the at least one conducting wire is fixed to the at least one electrode contact at a point located underneath the at least one electrode contact.

4. The implantable electrode device of claim 1, wherein the first layer has a first surface and a second surface, wherein the second layer is arranged on the first surface, and wherein the first opening is formed in the second surface of the first layer.

5. The implantable electrode device of claim 4, wherein the strain relief means is one of a suture, a string, litz wires, or other elongated, flexible, high pull-strength element.

6. The implantable electrode device of claim 1, wherein the core comprises a filling material made from silicone.

7. The implantable electrode device of claim 1, wherein the second layer is made from a polymer.

8. The implantable electrode device (1) of claim 1, wherein the core comprises a neutral fiber of the electrode device.

9. The implantable electrode device of claim 1, wherein the implantable electrode is formed as a micro-electrode array.

10. The implantable electrode device of claim 9, wherein the micro-array comprises a plurality of electrode contacts.

* * * * *